United States Patent [19]

Hink et al.

[11] Patent Number: 4,933,371

[45] Date of Patent: Jun. 12, 1990

[54] CONTROLLING TICKS AND FLEAS WITH LINALOOL

[75] Inventors: W. Fredric Hink, Columbus, Ohio; Thomas E. Duffey, Tequefta, Fla.

[73] Assignee: Shirlo, Inc., Memphis, Tenn.

[21] Appl. No.: 235,073

[22] Filed: Aug. 23, 1988

Related U.S. Application Data

[63] Continuation-in-part of Ser. No. 634,903, Jul. 26, 1984, abandoned.

[51] Int. Cl.$^5$ ............................................. A01N 31/00
[52] U.S. Cl. ..................................... 514/739; 514/875; 514/880; 514/881
[58] Field of Search ............... 514/739, 875, 880, 881; 424/45

[56] References Cited

U.S. PATENT DOCUMENTS 4,379,168  4/1983  Dotolo ................................ 514/753

OTHER PUBLICATIONS

R. N. Sharma et al., "Orientation and Developement Inhibition in the Houseflys by Certain Terpenoids" J. Med. Eng., vol. 11, No. 5, pp. 617–621.

*Primary Examiner*—Douglas W. Robinson
*Assistant Examiner*—Zohreh A. Fay
*Attorney, Agent, or Firm*—Sroufe, Zamecki, Payne & Lundeen

[57] ABSTRACT

Method of treating animal hosts or their environment for ticks and fleas by applying thereto a toxic amount of linalool.

14 Claims, No Drawings

CONTROLLING TICKS AND FLEAS WITH LINALOOL

BACKGROUND OF THE INVENTION

This is a continuation-in-part of application Ser. No. 634,903, filed July 26, 1984, now abandoned.

This invention relates to methods for controlling ticks and fleas, more particularly to such methods which employ pesticides comprising linalool to control tick and flea infestations on animals and to pesticidal compositions useful in the practice of that method.

Use of synthetic pesticides or insecticides which are naturally occurring compounds has become undesirable in many instances. Synthetic insecticides can be toxic not only to the pest but also to animals or people to be protected from the pest. Further, the Federal Insecticide, Fungicide and Rodenticide Act has made registration and use of synthetic insecticides somewhat difficult. Compliance with regulations requires, among other things, Environmental Protection Agency approval.

Use of naturally occurring, or so-called "organic" insecticides is desirable in many other respects. Many of these insecticides have proven to be safe to humans and the animals whom they are to benefit. However, their ability to satisfactorily control ticks and fleas is extremely limited. As is well known, ticks and fleas are more difficult to control than other insects and like pests by insecticides.

This invention employs linalool, a naturally occurring acyclic terpene alcohol, as the essential pesticide for controlling ticks and fleas.

Linalool occurs naturally in more than 200 oils from flowers, wood, leaves and herbs. It is found in oils of Ceylon's cinnamon, sassafras, orange flower, bergamot, *Artemisia balchanorum*, ylang ylang, rosewood and other oils. Linalool is commonly used as a flavoring agent and a perfume. Linalool is also known as lily of the valley scent. Linalool is also known as coriandrol and 3,7-dimethyl-1,6-octadiene-3-ol. It has a significant and surprisingly different spectrum of insecticidal activity compared to other terpenes having the same basic structure.

Linalool may be obtained directly by fractional distillation from vegetable products. It can also be obtained synthetically from other monocyclic terpenes. It can be distilled from commercial d-limonene, the commonly available form of which may comprise on the order of 95 percent pure d-limonene and approximately seven other component oils.

A few terpenes have been found to have some insecticidal activity. Terpenes are found in essential oils of plants and come in many forms. Terpenes are discussed in Vasechko et al., G. I., *Insecticidal Properties of Some Components of Essential Oils,* Dopovidi, Akademiya, Nauk Ukrayins'koyl RSR, Volume 32, 1970, pp. 275–278, and abstracted at *Chemical Abstracts,* 74(9)413772. Terpenes such as borneol and alpha terpineol were found to have toxicity for cockchafer mealworm larvae. Another publication discussing terpenes is Smelyanets, V. P., *Toxicity of Some Terpene Compounds,* abstracted at *Chemical Abstracts,* 70, 35483(g). The toxicity of cyclic hydrocarbon terpenes for the pine bugs, including terpineol and of cyclic terpene alcohols and their acetates and its acetate and chacetate and bornyl acetate was discussed. The article states that, "It was of interest to make a study of these compounds and of those frequently encountered in other essential oils—menthol, linalool, borneol, and their acetates", but does not indicate whether or not linalool was tested as an insecticide. The publication further states that "the results of the experiments indicate that terpene compounds exert a dissimilar influence on harmful insects of various species; this yields the possibility of selecting, for some, attractants, and for others—repellents, without causing harm to useful insects." The cyclic terpene hydrocarbon D-limonene is disclosed in U.S. Pat. No. 4,379,168 as the insect killing ingredient in a pesticide. U.S. Pat. No. 3,705,941 corresponding to Fr. Demande No. 2,068,820, cited at 77:57618b, lists (col. 12, lines 55–73) linalool as an "additive material" (col. 11, lines 24–30), viz., an odorant (col. 24, lines 58–62), to an insecticidal composition containing a phosphoric acid ester or thionophosphoric acid ester as the essential insecticidal ingredient. Sharma et al., in J. Med. Entomol. 1974, 11:5,617–621, describes the orientation and developmental inhibition activity in the housefly by various terpenoids, including linalool. In terms of acute movability and % normal surviving adults, linalool was considerably less active than d-limonene (10% vs. 20.0% and 50% vs. 18.3%, respectively, at 40 ug/larva). However, in terms of repulsion of trapped flies and % inhibition of egg hatching, the opposite was true (53.9% vs. 15.1% and 42.2 vs. 20%, respectively, at 0.02 $mg/cm^2$).

Linalool has also been found to be attractive to some insects such as the silkworm and cotton leafworm larvae, while being relatively ineffective as a repellant for the mosquito, D. L. J. Opdyke (ed.) *Monographs on Fragrance Raw Materials,* p. 501 (Pergamon Press; New York, N.Y., 1979).

It is well known in the prior art that the control of ticks and fleas is especially difficult, in part because pesticides which are effective against these pests are toxic to pets infested with them.

The prior art did not recognize the exceptional ability of linalool to control ticks and fleas, although its insecticidal activity against houseflies and other insects had been reported.

In accordance with the present invention, it has been found that linalool is an extremely effective pesticide for controlling ticks and fleas, which may be used in a variety of ways and in a variety of pesticide compositions. It has also been found to be effective in killing a variety of other insects and insect forms, including house flies and mosquitoes, various insect eggs and larvae, ticks, spider mites and spider mite eggs.

Linalool is highly acceptable for domestic use, both directly on domestic animals and on rugs, carpets and furniture in environments frequented by a household pet.

Linalool combines well with other ingredients of the different forms of insecticides provided in accordance with the present invention.

OBJECTS OF THE INVENTION

It is an object of the present invention to provide a method of killing and otherwise controlling ticks and fleas employing linalool as the essential pesticide.

It is another object of the present invention to provide such a method which employs a dip, spray or shampoo comprising linalool.

It is also an object of the present invention to provide novel pesticidal compositions comprising linalool as the essential pesticidal ingredient, adapted for killing adult fleas and ticks and their larvae and eggs, and other like blood-sucking pests.

Upon further study of the specification and appended claims, further objects and advantages of this invention will become apparent to those skilled in the art.

SUMMARY OF THE INVENTION

In a method aspect, this invention relates to a method of treating an area infested with ticks or fleas, which comprises applying to the affected area an amount of linalool effective to kill the infesting ticks or fleas.

In a preferred method aspect, the area to which the linalool is applied is the coat of an animal and the linalool is preferably applied as a shampoo, dip or spray.

In other method aspects, linalool is employed to control other flying pests, e.g., flies or mosquitoes, and crawling pests, e.g., fire ants and other insects and arachnids.

In composition aspects, this invention relates to novel pesticidal compositions adapted to the practice of the methods of this invention.

DETAILED DESCRIPTION

Linalool in its pure form is a viscous liquid. It may be combined with various vehicles. It is soluble in many alcohols and alcohol-water combinations. As used herein, unless otherwise specified, the term "alcohol" means ethanol. Alcohol, both aqueous and denatured, is a useful solvent for spray purposes. For use as an insecticidal shampoo, for example, a dog or cat flea shampoo, linalool may be dispersed as an aqueous or alcoholic liquid composition comprising a surfactant. It is combinable with vehicles for many known useful insecticidal compositions to form useful products such as sprays, dips, shampoos and the like. For example, in controlling and killing fleas and ticks on their animal host, a pesticidally effective amount of linalool effective to kill the fleas and ticks is applied to the skin and hair of the animal. In the form of a spray, the spray is formulated to be used in an undiluted form and directed onto the hair and skin of a canine, feline or other animal, e.g., horses, cattle or other farm animal. Pump or aerosol sprays can be employed for use on plants or in home application as well as for veterinary use. Shampoos are used in the conventional manner.

Insecticides and pesticides can be formulated with linalool concentrations ranging from about 0.1 to about 95 percent by weight, with final concentrations (as applied) preferably being in the range from about 0.5 to 5%. Although the optimum linalool concentrations depend on whether the linalool is applied as a shampoo, a dip, a pump spray or an aerosol, concentrations effective to contact the affected area with about 25-150 ug/cm$^2$ are preferred, e.g., 0.5-5% concentrations, especially 1-4% in the case of dips and pump sprays and 0.5-2% in the case of shampoos. The linalool can be combined with an inert vehicle or carrier, including conventional vehicles, surfactants, stabilizer, perfumes and the like. Linalool can be formulated with other insecticides and/or synergists in an inert carrier medium.

In one embodiment of the invention, the linalool is applied to the skin and coat of the host infested with or susceptible to infestation with fleas and/or ticks or other blood-sucking pest in the form of a pesticidal shampoo. The shampoos ordinarily comprise about 0.5 percent to about 10 percent linalool, with about 0.5 percent to about 5.0 percent being preferred. A preferred shampoo base contains about 20-70 percent surfactant or emulsifier, which may be any suitable surfactant of the anionic, cationic, non-ionic or amphoteric type. It is also preferred to incorporate in the shampoo base one or more of about 0.01-5 percent of an emollient which may be any emollient suitable for use on the coats of animals; about 0.01-5 percent lanolin oil or a lanolin derivative; and/or about 0.01-10 percent of a foaming agent, e.g., an amide foam builder, e.g., a coconut diethanolamide. The remainder of the shampoo base is usually water and, if desired, materials for other desired functions, such as perfumes, detergents, thickening agents, stabilizers, emulsifiers, preservatives, antioxidants, etc. These shampoo compositions are particularly effective in killing fleas and ticks on the skin or in the hair of the animal host, especially when they are left on the hair or fur for 5 minutes or longer, e.g., from 5 to 15 minutes.

Linalool is highly effective in a number of pesticidal shampoo compositions. The pesticide shampoo composition is applied on the skin and hair of an animal in a conventional manner. In the following examples various shampoo components are used alone with the linalool. Commonly available shampoo bases may be used.

An exemplary suitable shampoo base comprises:
20-70% surfactant, e.g., triethanolamine lauryl sulfate (40% active) by weight
0.01-05% lanolin derivative
0.01-05% emollient
0.01-10% amide
0-10% thickening agent
Balance: water, stabilizers, preservatives.

Other anionic surfactants such as sodium lauryl sulfate, sodium alpha olefin sulfonate, ammonium lauryl sulfate, and similar surfactants may be used in lieu of triethanolamine lauryl sulfate. Amphoteric surfactants may be used instead of, or in conjunction with, an anionic surfactant. Further, nonionic surfactants may be used in place of, or in conjunction with, anionic surfactants.

The lanolin derivative employed in the exemplary shampoo formulation can be lanolin oil, which is the liquid fraction of whole lanolin obtained by physical means, or any number of ethoxylated polymers of whole lanolin products, such as Lanogel 41, Lanogel 21 (Rosinson-Wagner Chemical Company), or Ethoxylan 50 (a product of Malstrom Chemical Company).

In the shampoo formulations, any emollient, such as glycerine, isopropyl myristate or Finesolv TN can be used. Finesolv TN (Finetex, Inc.) is a benzoate alcohol having twelve to fifteen carbon atoms.

The amide employed in the Exemplary Example formulation may be Marsamid 50 (a product of AZS Chemical Company) a coconut diethanolamide, or other coconut diethanolamide products such as Monamid® 150-ADD (Mona Chemical Company) or Emid® 6515 (Emery Chemical Company).

Examples of thickening agents which are used, are Methocel 65HG (a methylcellulose product of Dow Chemical Company), hydroxypropyl methylcellulose of similar compounds, such as the hydroxyethyl celluloses, e.g., Cellosize® QP of Union Carbide or Natrosol® 250 of Hercules Powder Company.

In another embodiment of the invention, the linalool is applied to the affected animal as an animal dip.

A dip composition containing an amount of linalool toxic to ticks and fleas can be employed in which an animal hosting fleas and/or ticks can be bathed by applying the dip composition to the skin and hair of the animal hosting fleas and ticks and wetting the animal completely with the dip composition. The dip is preferably provided as a concentrate, e.g., one which consists essentially of linalool in an amount of at least about 10 percent by weight with at least about 10 percent surfactant. The linalool is utilized as the essential pesticidally active toxic ingredient. Preferably, the pesticide dip concentrate contains from about 10 percent to about 90 percent linalool, with about 90 percent to about 10 percent of a surfactant, which may be any anionic or non-ionic surfactant capable of dispersing the linalool in water. A pesticide dip concentrate can be prepared containing about 10 to about 90 percent linalool together with at least about 10 percent of a surfactant such as Tween® 80; Sponto® 232T; Sponto® 234T; Tween® 20, or similar anionic and non-ionic surfactants. Also, dip concentrates of this invention can contain a solvent such as xylene, or other aromatic solvent, aliphatic solvent, mineral spirits, or water. The dip concentrate is ordinarily diluted with water just prior to use.

The concentrate can be highly diluted by adding water to prepare the dip composition thereby reducing the concentration of the toxic amount of linalool to the desired concentration range for the dip composition. A preferred dilution is 1 to 4 fluid ounces concentrate per gallon of water. The desired dilution will vary based on the concentration of linalool in the concentrate. Dilution of the concentrate should achieve a final linalool concentration of about 0.1 percent to about 2.5 percent, preferably from about 0.3 percent to about 1.5 percent and most desirably from about 0.3 percent to about 1.0 percent for application to the skin and hair of the animal. Storage in diluted form over a long period of time, e.g. several months, may result in some loss of activity. The diluted dip composition also is an effective insecticide when applied to fire ant mounds or when used as a yard spray.

In another embodiment of this invention the linalool form is applied as a spray to the coat of domestic animals, (e.g., dogs and cats, or to their environment such as bedding, carpets and furniture in a room infested with fleas or like blood sucking pests. The concentration of linalool is at least about 0.1 percent, e.g. from about 0.1 to 15 percent, with about 1 percent to about 5 percent preferred, most preferably about 1 percent to about 2 percent. The remainder of this spray composition can be any conventional carrier suitable for application to the intended environment, e.g., a solution of water and alcohol.

A pump spray is a liquid for use in a hand-held container for spraying directly onto the coat of an animal, and/or onto bedding, carpets and other environmental surfaces. For direct application to the animal, an amount of mist of the liquid is sprayed onto the skin and hair of the animal sufficient to impart a moist feel to the coat. The optimum dose is dependent upon size and hair length. In use, a toxic amount of the pump spray composition is sprayed onto the animal's coat and is permitted to remain there. Killing of fleas occurs both upon direct contact of the spray on fleas as well as contact by the fleas with the wetted coat or with linalool vapors. The pesticide pump spray compositions contain at least 0.1 percent linalool dissolved or dispersed in a liquid carrier, e.g., from about 0.1 percent to about 15 percent, with about 1 percent to about 5 percent preferred, and a range of about 1 percent to about 2 percent being presently most preferred. Ethanol provides a suitable vehicle or liquid carrier in which to dissolve linalool, carry it as a spray and it can be left on the animal's coat until it evaporates. In the pump spray examples below, ethanol is provided in the form of a specially denatured alcohol, in particular, SDA-40, which contain ⅛ gallon t-butyl alcohol and 1½ adv. ounces of either (1) brucine alkaloid, (2) brucine sulfate NF IX, (3) quassin or, (4) any combination of two or of three of those denaturants per 100 gallons of ethanol. Diluted ethanol, i.e., aqueous alcohol, can also be used. Other denatured alcohols may be used. Saturated alcohols other than ethanol may also be employed as a solvent for linalool, but ethanol is preferred.

To enhance the toxicity of the linalool, insecticidal synergists, e.g., sesame oil or piperonyl butoxide, may be employed in the linalool compositions of this invention. At synergist concentrations of about 0.25 percent to 0.50 percent, the percentage of linalool may be reduced very substantially with no reduction in its pesticidal efficacy, as illustrated in the examples and data herein. Propylene glycol, e.g., at concentrations of about 10% to about 15%, enhances the pesticidal toxicity of the linalool compositions.

The shampoos and pump sprays of this invention are also useful in the elimination of common head lice and other pests which infest the hair or skin of humans.

Aerosol spray compositions embodying linalool are highly effective in killing fleas in a household environment.

The present invention provides linalool insecticides, larvacides and ovicides and method of using them as such, e.g., for the treatment of animals bearing fleas or ticks on their skin or in their hair and the treatment of environments infested therewith, to rid the animals and the environment of such pests. Further, the linalool employed in the methods of this invention may be employed in a wide variety of forms at varying concentrations of linalool to provide effective toxicity under different conditions of application and/or for use upon different kinds of insects and other pests.

Carpet sprays having useful pesticidal activity against fleas, ticks and other pests, their larvae and eggs employed in this invention may be conveniently formulated as a pesticide carpet spray concentrate comprising about 10 to 20 percent linalool, with about 10 percent to about 15 percent linalool being preferred, in a vehicle capable of rendering the linalool miscible in water. A preferred concentrate contains about 10 percent linalool, 40 percent Witconate P10-59 and 50 percent Witconol NP100. For use as a pesticide carpet spray, this concentrate may be diluted with water or aqueous alcohol to obtain the desired final concentration of about 0.5 percent to about 2.0 percent linalool. Usually the concentrate is formulated for dilution with about 10 to 20 parts water per part concentrate. "Witconate" and "Witconol" are trademarks of Witco Chemical Company. Witconate P10-59 is an anionic surfactant which is an amine salt of dodecylbenzene sulfonic acid. Witconol NP 100 is a nonionic surfactant, viz., a nonylphenol polyethylene glycol ether.

In the following examples, spray formulations are provided as concentrates. At the time of application, each concentrate can be diluted as needed to produce the desired final pesticide carpet spray concentration, usually from 10 to 1 to 20 to 1 by weight with water for application to a carpet. The resulting liquid spray composition is sprayed onto the carpet to wet each of the pests, such as fleas and ticks and their larvae and eggs harbored therein. The liquid spray composition contains linalool as the essential pesticide in an amount ranging from about 0.5 percent to about 10 percent, preferably from about 0.5 percent to about 2.0 percent, at least one surfactant, in an amount ranging from about 1 percent to about 10 percent, and water, in an amount ranging from about 98 percent to about 80 percent. The degree of saturation required for carpets is somewhat analogous to that for shampoos or sprays. The length and density of the carpet pile dictate the amount of spray required.

Aerosol spray formulations embodying linalool as a pesticide have been found to be effective in killing blood sucking pests, such as fleas and ticks, and to be particularly effective against fleas. In aerosol spray compositions, linalool is usually present in a concentration from about 1% to about 15% along with about 8% to about 20% propane as propellant and the balance 1,1,1-trichlorethane as vapor pressure depressants. In one formulation, the linalool is provided at about 10% concentration with 2.5% piperonyl butoxide as a synergist, about 14% propane as a propellant, about 32% methylene chloride as a solvent, and the balance 1,1,1-trichlorethane, as an additional solvent. Another formulation employs a mixture of 1.11% linalool, 0.29% Dursban ® (chlorpyrifos, an insecticide manufactured by Dow Chemical Co.), 0.56% piperonyl butoxide, 0.6% Arylene Gamma (fragrance), 13.33% isopropyl alcohol and 84.65% 1,1,1-trichlorethane.

As stated above, the toxicity of linalool, e.g., with respect to adult fleas, can be enhanced by combination with a pesticidal synergist, such as sesame oil or piperonyl butoxide, another pesticidally active terpene, e.g., dl- or d-limonene, α-terpinol, carvacrol, citronellal, eugenol, citral, geraniol or camphene. At concentrations of 0.25 percent to 0.5 synergist, the percentage of linalool may be reduced very substantially with no reduction in insecticidal efficacy, as illustrated in Examples XXVII and XXVIII.

The linalool compositions of this invention are also highly effective in combatting fire ant infestations in fields.

A fire ant insecticide composition for treating areas infested therewith, e.g., fire ant mounds, embodying this invention can be formulated as a fire ant treatment concentrate comprising about 2 percent to about 20 percent linalool by weight in a surfactant capable of rendering the linalool miscible in water. The concentrate is diluted to the desired concentration of linalool by adding water. The minimum final concentration of linalool is at least 0.1 percent by weight in the resulting fire ant insecticide composition. After dilution with water, the final linalool concentration preferably ranges from about 0.3 percent to about 1.5 percent by weight. The insecticide composition with a pesticidally effective toxic amount of linalool is than applied on the fire ant mound so as to contact the fire ants with the insecticide composition, thereby controlling and killing same.

Linalool has also been found effective in controlling and killing spider mites and spider mite eggs by contacting them with a composition of this invention.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, unless otherwise indicated, all parts, percentages, proportions and ratios are by weight.

The entire text of all applications, patents and publications, if any, cited above and below are hereby incorporated by reference.

EXAMPLE I

A pesticide shampoo is provided comprising 1 percent linalool by weight in a shampoo base. In use on test animals it provided flea kill almost instantly, e.g., in approximately three minutes. The linalool had rapid pesticidal effect and the hair remained easy to brush. After wetting an animal hosting fleas and ticks with water, the shampoo comprising an effective toxic amount of linalool in a shampoo base is applied to the skin and hair of the animal host. The shampoo is worked into a lather. Substantially the entire skin and hair of the animal is wetted and contacted with the lather for a time interval up to 15 minutes and preferably at least about 5 minutes before rinsing the lather from the skin and hair of the animal with water.

The shampoo base used in this Example is:
50% Triethanolamine lauryl sulfate (40% active)
5% Amide
2.5% Glycerine
2.5% Lanolin derivative
1.0% Stabilizer
Balance: Water In this shampoo base, the triethanolamine lauryl sulfate used in this Example is available under the trademark Standapol ® T, an anionic surfactant which is a product of Henkel Corp. The amide is Marsamid 50 (AZS Chemical Company) and the lanolin derivative of this Example is Lanogel 41 (Robinson-Wagner Chemical Company). As a stabilizer, we provided in this shampoo base Tween ® 80, a nonionic polyoxyalkalene derivative of hexitol anhydride partial long chain fatty esters, a product of ICI Americas, Inc. "Tween" is a registered trademark of ICI Americas, Inc.

Reference to a "shampoo base" in the following examples refer to the shampoo base composition of this Example I.

EXAMPLE II

A shampoo is provided comprising 1 percent linalool, 5.3 percent d-limonene and the balance shampoo base.

The flea kill remained fast, but this example did not lather as well as the formulation of Example I. The composition was perceived to be substantially odorless.

EXAMPLE III

The shampoo comprised 0.5 percent linalool and 3.0 percent d-limonene in a shampoo base. The killing time for fleas was longer in this example but nonetheless was under ten minutes. Lathering characteristics of the shampoo were not adversely affected and the odor was perceived to be pleasant.

EXAMPLE IV

Higher percentages of linalool can also be utilized, for example, a shampoo comprising 5 percent linalool, 38 percent water and 57 percent shampoo base.

EXAMPLE V

The following is another example of a shampoo concentrate.

| Ingredient | Wt % |
| --- | --- |
| Linalool 925 | 4.08 |
| Sipon LT6 (foaming agent; Alcolac Chemical) | 50.00 |
| Glycerine USP | 2.50 |
| Marsamid 50 (foam stabilizer; AZS Chemical) | 5.00 |
| Tween 80 (stabilizer) | 1.00 |
| Silicone ® 193 | 1.00 |
| Lanogel 41 (lanolin) | 2.50 |
| VitaCos 535 (antiirritant; Wickhen Products) | 0.25 |
| Arylene Gamma D8364 | 0.10 |
| Citric Acid | 0.32 |
| Water (deionized) | 33.25 |
| | 100.00% |

Mix about two-thirds of the water (hot) with the Sipon LT6 and the glycerine. Add successively the linalool, Marsamaid 50, Tween 80, Silocone 193, Lanogel 41, VitaCos 535, Arylene Gamma D8364 and mix for one hour. Adjust the pH to 7 with citric acid and add remaining water.

EXAMPLE VI

A further modification of the formulas for linalool containing shampoos to provide desirable fragrance properties of citrus oils comprises a shampoo formulated as follows:

| | | |
| --- | --- | --- |
| 5% | linalool | |
| 0.25% | citric acid | |
| 0.25% | "Fresh lime" fragrance (Arylessence Inc.) | |

The remainder of this composition comprises the shampoo base of Example I diluted with water in a ratio of 70 percent shampoo base to 30 percent water.

EXAMPLE VII 94 percent of a 50:50 mixture of water and shampoo base was combined with 5 percent linalool and 1 percent methanol. The resulting shampoo composition was found to be an effective pesticide when applied to the coats of animals.

EXAMPLE VIII

Pesticidal efficacy was also achieved with a shampoo comprising 1 percent linalool, 5 percent d-limonene and the remainder shampoo base.

The shampoos of Examples I–VIII kill all of the fleas and ticks on dogs when an amount thereof effective to provide a full lather on their wet fur is left thereon for at least 10 minutes. Shorter times, e.g., the normal time required to shampoo a dog (with two applications of the shampoo) are also effective but a 100% kill is not always achieved.

EXAMPLE IX

A highly effective pesticide pump spray was provided comprising 5 percent linalool and 95 percent of a solution of water and SDA-40 by weight. Initial killing power and prolonged killing power over a 24-hour period was provided at saturation levels of 25, 50 and 75 percent. The saturation levels are subjective measures of the degree to which an animal's coat is wetted with spray.

EXAMPLE X

Insecticidal efficacy was also achieved with 5 percent linalool and 95 percent SDA-40 as a spray.

EXAMPLE XI

Pesticidal efficacy was also achieved utilizing 1 percent linalool as a spray dissolved in 99 percent denatured ethanol (SDA-40).

EXAMPLE XII 1 percent linalool was also effective as a spray in a composition in which the remaining 99 percent was water and SDA-40 in weight ratio of 3 to 7, respectively.

Linalool can also be used with other terpenes which have toxicant properties as illustrated in Examples XIII and XIV.

EXAMPLE XIII

A spray was provided comprising 1 percent linalool, 1 percent alpha-terpineol and 98 percent SDA-40. At nominal saturation levels, e.g., 50 percent, for a given hair length, a fast kill, namely, under 10 minutes, was accomplished. The odor of the spray was stronger than that for Examples XI and XII, however.

EXAMPLE XIV

A pump spray was provided comprising 0.5 percent linalool, 5.43 percent d-limonene and 94.07 percent SDA-40. Effective kill was provided and the composition was perceived by testers to have a good odor.

EXAMPLE XV

In this example, the amount of linalool was increased and the amount of SDA-40 was decreased in a pump spray consisting of 1 percent linalool, 5.43 percent d-limonene and 93.57 percent SDA-40. Again, good kill and good odor were reported. 1% linalool is also an effective flea and tick pump spray in admixture with 1% d-limonene, 0.50% piperonyl butoxide, 10% propylene glycol and 0.5% perfume, in 87.45% SDA-40 denatured alcohol as a vehicle.

EXAMPLE XVI

The composition of Example XV was duplicated with the exception that 0.5 percent by weight of the SDA-40 was replaced with Vita Cos 535, a form of wheat germ glycerides. Vita Cos is a trademark of Wickhen Products, Inc. Both effective kill and pleasant odor were reported. Additionally, the animals' coats were left with a good shine when brushed out after drying of the spray.

The sprays of Examples IX–XVI are effective to kill fleas and ticks on dogs, cats, and farm animals when their coat and skin are moistened therewith.

EXAMPLE XVII

A dip concentrate was provided comprising 10 percent linalool, 75 percent d-limonene and 15 percent Tween ® 80. The Tween 80 is a surfactant which renders the terpene oils miscible in water. When diluted as described herein by admixing 1 to 2 ounces in a gallon of water, the solution stayed clear. Highly effective flea kills were reported along with satisfactory drying characteristics.

Other surfactants may be substituted for Tween 80. Tween 80 is a registered trademark of ICI Americas, Inc., for nonionic polyoxyalkylene derivative of hexitol anhydride partial long chain fatty acid esters.

EXAMPLE XVIII

A pesticide dip concentrate was also prepared comprising 90 percent linalool and 10 percent Tween 80. Highly effective pesticide dip compositions were produced by diluting this concentrate at ratios from about 1 ounce to about 2 ounces per gallon of water.

The following is an example of an emulsifiable dip concentrate which is highly effective (100% kill of fleas with no survivors after 4 hours) when used at a rate of 3 oz./gallon of water:

| Ingredient | Wt% |
|---|---|
| Linalool | 40% |
| piperonylbutoxide | 40% |
| propylene glycol | 10% |
| citrus fragrance | 1% |
| Sponto 234* | 4.5% |
| Sponto 232* | 4.5% |
| | 100.0% |

*emulsifier, Whitco Chemical, Houston, Texas.

EXAMPLE XIX

Linalool dip concentrates may also be formulated with reduced linalool concentrations. A dip concentrate was provided comprising 5 percent linalool, 10 percent Tween 80, 30 percent farnesol and 55 percent castor oil. Since the farnesol component functions as both a perfume and as an insecticide, the range of dilution can be the same as in prior dip examples with comparable effective results.

The dips of Examples XVII–XIX are effective to kill and repel ticks, fleas and like blood sucking pests on dogs, cats and farm animals when the animal's skin and hair or fur are wet therewith.

EXAMPLE XX

A carpet spray concentrate was provided comprising 10 percent linalool, 10 percent alpha-terpineol, 40 percent Witconate P10-59 and 40 percent Witconol NP-100. P10-59 comprises the amine salt of dodecylbenzene sulfonic acid. Np-100 comprises nonylphenol polyethylene glycol ether. When diluted as provided above, the resulting sprays were found to be effective insecticides.

EXAMPLE XXI

Insecticidally effective spray was provided wherein the amounts of terpene compounds in Example XIX were doubled with proportional reductions in the other components identified. In the above-described examples, the most active species of terpene where there is a combination of terpenes has been found to be linalool.

Tables 1 and 2 which follow set forth the results of testing for contact pesticidal activity of linalool against adult fleas and flea larvae.

TABLE 1

FLEAS PUT ON WET TREATED SURFACE
(Percentage Mortality Plus Immobility)

| Treatment | 5 min. | 10 min. | 15 min. | 20 min. | 60 min. |
|---|---|---|---|---|---|
| Linalool | 97% | 97% | 100% | 100% | 100% |
| Control (H$_2$O) | 0 | 0 | 0 | 0 | 0 |

The percentages are the sum of the percents of mortality and immobility (fleas on their side and can't walk). There were 27 to 36 fleas employed per treatment. The compositions employed had a final linalool concentration of 0.7% (stock solutions of linalool made up with 90% linalool and 10% Tween 80 and then diluted at 1 ounce per gallon or 1:128).

As illustrated in Table 2 below, linalool is also effective in varying concentrations to control and kill flea larvae by contacting them with an effective toxic amount of linalool. The concentration of the linalool employed affected the time required to achieve 100% mortality more than it affected mortality rate. Stock formulations were made up with 90 percent linalool and 10 percent Tween 80. The stock solutions were diluted with water to obtain the various concentrations set forth in Table 2. One milliliter of a diluted solution was put on a filter paper in a petri dish and flea larvae were then placed in contact with the thus-wet paper. There were 10 larvae employed in each test.

TABLE 2

TOXICITY OF LINALOOL TO FLEA LARVAE
(Percent Mortality)

| | Time After Start of Test | | | |
|---|---|---|---|---|
| | 5 min | 10 min | 15 min. | 30 min. |
| 10% Linalool | 70 | 70 | 100 | 100 |
| 5% Linalool | 30 | 80 | 100 | 100 |
| 2.5% Linalool | 10 | 30 | 90 | 100 |
| 1% Linalool | 10 | 30 | 60 | 100 |

TOXICITY OF WATER BASE SPRAYS AGAINST ADULT HOUSE FLIES AND MOSQUITOES

It has been found that a wide range of linalool concentrations may also be used in insecticides which are effective insecticidal and pesticidal sprays for killing adult house flies and mosquitoes.

A stock solution of linalool was prepared with 90 percent linalool plus 10 percent Tween 80. The stock was diluted with water to obtain 10 percent, 5 percent, and 2.5 percent linalool concentrations, respectively, in the insecticide.

The adult insects were placed in cylindrical cartons with screen lids. The insecticide spray containing an effective amount of linalool was sprayed through the screen using a glass chromatogram sprayer to contact the adult fleas and mosquitoes therewith. To simulate open room conditions, 3 to 5 minutes after being sprayed, the insects were transferred to dry filter paper in petri dishes. By so doing, the fleas and mosquitoes were removed from the slightly moist spray container and contact with the linalool.

There were 10 house flies and 7 to 10 mosquitoes employed for each treatment. The results are set forth in Table 3.

TABLE 3
TESTS AGAINST ADULT HOUSE FLIES AND MOSQUITOES WITH LINALOOL SPRAYS

House Flies

| Linalool Concentration | Results |
| --- | --- |
| 10% | All immobile at one minute, 100 immobile at 5 minutes and 100% mortality at 5 minutes. |
| 5% | 80% immobile at 2 minutes, 100 percent paralyzed at 10 minutes, partial recovery by 30 percent which buzzed around on their backs at 30 to 60 minutes, but all eventually died. |

Mosquitoes

| % Linalool Concentration | Results |
| --- | --- |
| 10% | Instant "knock down," 100% never move and are dead immediately. |
| 5% | Instant "knock down," 100% do not move or recover. |
| 2.5% | 50% still move after 15 minutes. |

EXAMPLE XXII

A dip concentrate was prepared according to Example XVII. In use, the concentrate was diluted in the proportion of 1 fluid ounce to one-half gallon of water. One-half gallon of the diluted mixture was poured on an average sized fire ant mound (e.g. 10 inches in diameter by 6 inches). Insects touched by the liquid were highly agitated and began to evacuate the mounds. No living adults were found after 48 hours.

EXAMPLE XXIII

A dip concentrate was prepared according to Example XVIII and the concentrate was then diluted in the 10 proportion of 1 fluid ounce to ½ gallon of water. ½ gallon of this dilute mixture was poured on an average size fire ant mound as in Example XXII. As in the case of that example, no living adult fire ants were found after 48 hours.

Flea Ovicide

Linalool has been found to be effective with respect to flea eggs, as described in Example XXIV below.

EXAMPLE XXIV

A spray was provided with lanalool in the concentration of 0.5 percent in solvent (5.0% aqueous ethanol) and vehicle (0.1% Tween 80 in water). The eggs were placed in carpet squares. The spray was applied to carpet squares until the carpet was damp to the touch. The carpet squares were examined for live larvae at 11 days after treatment and for adult fleas at 24 days after treatment. In each case, 50 eggs of 1-16 hours of age were placed in each square. Neither live larvae nor adult fleas were found. The linalool spray prevented the flea eggs from developing.

Table 4 below sets forth the results of tests in which the toxicity of linalool to flea eggs in a carpet was compared with the toxicity of d-limonene at 1% concentrations.

TABLE 4
COMPARATIVE TOXICITY OF 1% D-LIMONENE AND 1% LINALOOL TO FLEA EGGS IN CARPET

| Number of Eggs Put in Carpet Squares | Treatment | Percent Adult Emergence |
| --- | --- | --- |
| 50 | 1.0 percent d-limonene | 68 |
| 48 | 1.0 percent linalool | 0 |
| 50 | Control - untreated | 62 |
| 57 | Control - water treated | 72 |

The formulations above were toxicant in a carrier consisting of 0.1 percent Tween 80 and the remainder was $H_2O$. Whereas the d-limonene exhibited no apparent toxicity to the flea eggs in the test, linalool exhibited 100% toxicity.

EXAMPLE XXV

A spray was formulated from a water solution of 0.1 percent linalool and 0.1 percent Tween 80. The spray was applied to leaves which were cut off of insect infested plants and put in petri dishes. The leaves were sprayed with a fine mist of the insecticide. A 100 percent mortality of spider mite eggs was achieved in the test.

EXAMPLE XXVI

A water solution of 0.5 percent linalool and 0.1 percent Tween 80 when sprayed onto leaves infested with spider mites, Example XXIV, achieved a 100 percent mortality.

It has been found that linalool at 1 percent or less has minimal phytotoxicity, and has little or no adverse effect on plants.

EXAMPLE XXVII

A mixture of 0.2 percent linalool and 0.5 percent sesame oil as a synergist in SDA-40 was provided and found to be effective as a spray when used in accordance with Example IX above.

EXAMPLE XXVIII

A pump spray with SDA-40 was prepared in accordance with Example IX above comprising 0.2 percent linalool and 0.5 percent piperonyl butoxide. 100 percent mortality against adult fleas was achieved.

The effectiveness of these additional components in combination with linalool is further illustrated in Table 5.

TABLE 5
TOXICITY OF LINALOOL SYNERGIZED WITH SESAME OIL OR PIPERONYL BUTOXIDE TO ADULT FLEAS

| | Mortality at these intervals[a] | | | | | |
| --- | --- | --- | --- | --- | --- | --- |
| Treatment | 5 min. | 10 min. | 15 min. | 20 min. | 60 min. | 24 hrs. |
| 0.2% linalool | 0% | 1% | 1% | 3% | 32% | 40% |
| 0.2% linalool + 0.5% sesame oil | 10% | 49% | 77% | 88% | 100% | 100% |
| 0.2% linalool + 0.5% piperonyl butoxide | 5% | 10% | 19% | 50% | 63% | 100% |
| 0.5% piperonyl butoxide (control) | 0% | 1% | 1% | 7% | 29% | 40% |
| 0.5% sesame oil (control) | 0% | 0% | 0% | 0% | 0% | 0% |

[a]mean values from 2 to 4 replicates.

From the above data it can be seen that where as the one hour post treatment mortality for 0.2% linalool plus 0.5% sesame oil was 100%, for 0.2% linalool plus 0.5% piperonyl butoxide it was 63% and for 0.2% linalool alone it was 32%.

TOXICITY OF LINALOOL VAPOR

In order to test the toxicity of the linalool vapors to fleas and other insects, a test apparatus was designed wherein the bottom of a vessel or chamber was covered with filter paper and a close fitting cover was placed over the chamber. A hole was drilled in the cover and a very fine mesh wire screen placed over the hole. A glass ring of 3 inches in height was placed over the screen and a cover placed over the glass ring. The glass ring was sealed to the top of the chamber.

The toxicant composition was pipetted onto the filter paper and insects or insect eggs were immediately put in the screen chamber. The toxicant composition used to generate the vapors was 0.2% or 1% linalool in an inert carrier consisting of 5.0 percent denatured alcohol, 0.1 percent Tween 80 and the remainder water. The results of the tests are set forth in Tables 6, 7 and 8.

TABLE 6

TOXICITY OF LINALOOL VAPORS TO ADULT FLEAS
(Percent Mortality Plus Immobility)

| Treatment | | | Number of Fleas | | |
|---|---|---|---|---|---|
| 1 percent linalool | | | 28 | | |
| 0.2 percent linalool | | | | | |
| Control - Untreated | | | 31 | | |

| Percent Linalool | Time (minutes) | | | | | |
|---|---|---|---|---|---|---|
| | 5 | 10 | 15 | 20 | 60 | 24 hrs. |
| 1.0 | 7 | 7 | 29 | 50 | 100 | 100 |
| 0.2 | 1 | 4 | 7 | 10 | 57 | 62 |
| Control (Untreated) | 0 | 0 | 0 | 0 | 0 | 0 |

TABLE 7

TOXICITY OF LINALOOL VAPORS TO FLEA LARVAE

| Treatment | Observations at 24 Hours |
|---|---|
| 5.0 percent linalool | 100 percent mortality |
| 2.5 percent linalool | 100 percent mortality |
| 1.0 percent linalool | 100 percent mortality |
| 0.5 percent linalool | 100 percent mortality |
| Control (5.0 percent denatured alcohol) | No mortality |
| Control (water) | 3 percent mortality |

In each of the treatments shown above, there were 25 to 30 larvae placed in the chamber above the screen. As in the previous example, the toxicant formula was linalool at the indicated percentage in an inert carrier consisting of 5.0 percent denatured alcohol, 0.1 percent Tween ® 80 and the remainder water.

TABLE 8

TOXICITY OF LINALOOL VAPORS TO FLEA EGGS

| Treatment | 48 hrs. | 72 hrs. |
|---|---|---|
| 1.0 percent linalool | 0.7% egg hatch (1 out of 150) | 4.7% egg hatch |
| Control - untreated | 56% egg hatch | 56% egg hatch |

In the above treatment of flea eggs, in each test 50 eggs were placed in the vapor chamber and the above data are the means from three replicates. The formula for the linalool used to generate the vapors was the same as that set forth in Table 6 above.

EXAMPLE XXIX

| LINALOOL AEROSOL |
|---|
| 10% Linalool |
| 2.5% Piperonyl Butoxide |
| 32% Methylene Chloride |
| 14% Propane |
| Balance: 1,1,1-trichlorethane |

In tests of the above aerosol, fleas were placed in open containers 10', 20' and 30' from a release point in an unoccupied residential house. In one test, in which a conventional amount of aerosol was released into the room, the percentage kill two hours after the fogger release was 56%, 80% and 84% for the 20 and 30 foot distances, respectively. In a second test at 10, 20 and 30 foot distances, the respective two hour kill rate was 88%, 92% and 96%.

ACTIVITY OF LINALOOL, D-LIMONENE AND α-TERPINEOL AGAINST FLEA EGGS, LARVAE AND PUPAE IN CARPET

At 10% and 5% concentrations, D-limonene, linalool, and α-terpineol all kill flea eggs in carpet. At 1.0% concentration, linalool and α-terpineol kill the eggs and completely eliminate the emergence of adults from the carpets whereas D-limonene alone does not.

Carpet was cut into 4 inch squares and put in 9 inch diameter glass dishes. The eggs, larvae or pupae were placed on the carpet and the nap was gently brushed with our fingers to ensure that the life stages settled down into the carpet. In the tests 50 eggs of known age (1–16 hrs. old), 50 late instar larvae or 50 pupae of known age (24–48 hrs. old) per carpet square were employed. After putting the selected stage into the carpet, the squares were sprayed with a course spray until they were damp. The carpet squares were permitted to dry for 24 hours at room temperature and then flea rearing medium was sprinkled onto the carpet so that the eggs or larvae therein could develop into adults, if alive. The dishes were then covered with mesh and put in incubators at 27° C. and 75% relative humidity.

The efficacy of the materials applied to the infested carpets was determined by counting the adult fleas that emerged from the eggs, larvae or pupae therein. For example, if 50 eggs were in the carpet and 25 adult fleas emerged, this would be 50% adult emergence. The egg tests were incubated for 8 weeks; the larvae for 8 weeks; and the pupae for 4 weeks. After these time periods no more adults emerge. After the first adults emerge, the dishes were checked every 3–4 days.

The results of the tests are given in the tables which follow. Because the experiments were done at different times, within a table there are several controls. All formulations are toxicant+5.0% EtOH+0.1% Tween 80 in water.

A surprising discovery was that flea eggs in carpet were easy to kill (Table 9). At 1.0% concentration, both linalool and α-terpineol were 100% effective and completely prevented eggs from developing into adults. Although D-limonene was not effective at 1% concentration, the addition of 0.5% MGK-264 to 1.0% D-limonene killed 100% of the eggs. MGK-264 synergist is also toxic to flea eggs (0.5% MGK-264 gave 2% adult emergence). The presence of MGK-264 rendered D-limonene, linalool and α-terpineol more toxic.

Linalool was the most toxic to flea larvae (Table 10). 1.0% linalool had only 10% adult emergence whereas D-limonene had 61% and α-terpineol had 36%. As with flea eggs, MGK-264 was toxic to the flea larvae. Addition of these to 1.0% D-limonene greatly increased the toxicity. They did not, however, increase the activity of 1.0% linalool.

For flea pupae, linalool and α-terpineol were more toxic than D-limonene (Table 11).

TABLE 9
TREATMENT OF FLEA EGGS IN CARPET

| D-limonene | Percent Adult Emergence |
|---|---|
| 10.0% | 0 |
| 5.0% | 0 |
| 1.0% | 62[a] |
| 1.0% + 0.5% MGK-264 | 0 |
| Linalool | |
| 10.0% | 0 |
| 5.0% | 0 |
| 1.0% | 0 |
| 0.5% | 64 |
| 1.0% + 0.5% MGK-264 | 0 |
| α-terpineol | |
| 10.0% | 0 |
| 5.0% | 0 |
| 1.0% | 0 |
| 0.5% | 56 |
| 0.5% MGK-264 | 2 |
| Controls (5.0% EtOH + 0.1% Tween 80 in $H_2O$) | |
| For 10.0% and 5.0% terpene tests | 48 |
| For 1.0% terpene tests | 72 |
| For MGK-264 tests | 58 |
| For 0.5% terpene tests | 64 |

[a]Mean of two replicates

TABLE 10
TREATMENT OF FLEA LARVAE IN CARPET

| D-limonene | Percent Adult Emergence |
|---|---|
| 10.0% | 0 |
| 5.0% | 0 |
| 1.0% | 61[a] |
| 1.0% + 0.5% MGK-264 | 10 |
| Linalool | |
| 10.0% | 0 |
| 5.0% | 0 |
| 1.0% | 10[a] |
| 1.0% + 0.5% MGK-264 | 31 |
| α-terpineol | |
| 10.0% | 0 |
| 5.0% | 0 |
| 1.0% | 36[a] |
| 0.5% MGK-264 | 28 |
| Controls (5.0% EtOH + 0.1% Tween 80 in $H_2O$) | |
| For 10.0% and 5.0% terpene tests | 65 |
| For 1.0% terpene tests | 75 |
| For MGK-264 tests | 58 |

[a]Mean of two replicates

TABLE 11
TREATMENT OF FLEA PUPAE IN CARPET

| D-limonene | Percent Adult Emergence |
|---|---|
| 10.0% | 30 |
| 5.0% | 20 |
| 1.0% | 24 |
| Linalool | |
| 10.0% | 0 |
| 5.0% | 0 |

TABLE 11-continued
TREATMENT OF FLEA PUPAE IN CARPET

| D-limonene | Percent Adult Emergence |
|---|---|
| 1.0% | 20[a] |
| α-terpineol | |
| 10.0% | 0 |
| 5.0% | 0 |
| 1.0% | 32 |
| Control (5.0% EtOH + 0.1% Tween 80 in $H_2O$) | 66 |

[a]Mean of two replicates

The tests conducted hereinafter were for the purpose of evaluating the toxicity of linalool to cat fleas.

Toxicity of Linalool to Eggs, Larvae, Pupae and Adult Cat Fleas

The toxicity of linalool to cat fleas (*Ctenocephalides felis*) was determined. Using in vitro techniques, linalool was equally toxic to eggs and adults whereas larvae were less susceptible. Fleas were eliminated from cats treated with a dip of 1.0% linalool or 0.5% linalool with synergist. Linalool acts rapidly on adult fleas and its activity is synergized by piperonyl butoxide. Since linalool has low vertebrate toxicity and high pesticidal activity to all flea life stages, it is useful in flea control programs as well as ridding them from animals infested with them.

Exposure of Adults, Larvae and Eggs to Linalool for $LC_{50}$ Determinations

In all tests, linalool (95%, SCM Organic Chemicals) was formulated with 5.0% EtOH and 0.1% Tween 80 in deionized water. Controls were 5.0% EtOH and 0.1% Tween 80 in water. For adults and eggs, plastic petri dishes (100×15 mm) were lined with Whatman #1 9.0 cm filter paper and 1.0 ml volumes of linalool were applied to the paper. For larvae, 15×7.5 cm glass crystallizing dishes were used with 15 cm Whatman #1 filter paper treated with 2.8 ml of the linalool solutions. These volumes saturated the papers, leaving no excess liquid. Adults were anesthetized with $CO_2$ and placed in an inverted petri dish lid. The paper in the bottom half of the dish was treated and inverted over the lid containing the anesthetized fleas. After they revived (about 1 minute), the entire dish was turned over, thus putting the adults in contact with the moist treated paper. At specific times after initial exposure, the adults were examined and considered dead if they did not move or were on their sides and unable to walk or right themselves. The $LC_{50}$ tests (the concentration at which the linalool was lethal to 50% of the flea form) were evaluated at 24 hours.

Larvae and eggs were transferred directly to linalool treated papers without prior exposure to $CO_2$. Third instar larvae were used and mortality read at 4 hours. For eggs, a small amount of rearing medium was put on after the first 24 hours. This was done so that if they hatched, the larvae would eat diet and not cannibalize other larvae or eggs. Egg tests were done at 27° C. and 75% RH using eggs of known age (1–24 hours) and egg hatch, the criterion for toxicity, was determined at 72 hours.

Dipping of Flea Infested Cats

To evaluate linalool on live, flea infested animals, a dip was formulated with 1.0 or 0.5% linalool, 5.0%

EtOH, and 0.5% emulsifier (Tween 80) in deionized water. Several days prior to treatment, the cats were infested with 200 newly emerged adult fleas. A total volume of 2 liters of each trial formulation was prepared. Cats were immersed in the "dip" and it was also poured over them to treat the head and dorsal aspect of the body. They were kept in the "dip" for 5 minutes to ensure thorough wetting of haircoat and then lightly blotted with towels to remove excess dip. After placing them back in their cages, pans underneath the cats were checked at intervals for the presence of dead adult fleas, eggs or adult flea feces. The absence of eggs and flea feces is reliable evidence that an animal is flea-free. The cats were also evaluated for the presence of adult fleas by careful visual examination.

$LC_{50}$ values were estimated by probit analysis. Fiducial limits were calculated at the $P<0.05$ level and are given in parentheses after the $LC_{50}$ values. Significant differences between $LC_{50}$ values were determined by nonoverlap of 95% fiducial limits. There was no mortality in the controls.

For each $LC_{50}$, 4-6 dosage levels were tested; each dosage was replicated 3 times, with 25-30 adult fleas or 25 eggs and larvae per replicate.

The results of the above tests are set forth below.

Linalool Toxicity to Life Stages

The dosage-mortality responses of adults, larvae, and eggs reveal that these stages have different sensitivities to linalool. The $LC_{50}$ for adults is 39 $\mu g/cm^2$ (27-48 $\mu g/cm^2$), for larvae it is 164 $\mu g/cm^2$ (154-172 $\mu g/cm^2$), and for eggs it is 38 $\mu g/cm^2$ (16-68 $\mu g/cm^2$). At the $LC_{50}$ level, the adults and eggs are equally susceptible. However, since the response line for eggs was flatter (slope=1.21, SEM±0.29) than that of adults (slope=9.20, SEM±2.14), there was greater heterogeneity in the egg population response to linalool. Of the 3 stages, the larvae are least susceptible and the linalool $LC_{50}$ was approximately 4 times that of the adults and eggs. Similar relative sensitivities of larvae and eggs were detected in the carpet tests. Compared to D-limonene, another natural product (Hink and Fee, J. Med. Entomol. 1986, 23:400-404), linalool is 4 times more toxic to adults and 1.4 times more toxic to larvae.

Sharma and Saxena, (J. Med. Entomol. 1974, 11:617-621), reported quantitative data on the toxicity of linalool to the common house fly (*Musca domestica*) eggs and larvae. Eggs were exposed to linalool by applying 0.1 ml acetone solutions to 1.0 mm layers of water in petri dishes and adding freshly laid eggs to the dishes. Although egg $LC_{50}$s were not determined, 100, 40, and 20 $\mu g/cm^2$ concentrations produced 76, 59, and 42% mortality, respectively. It thus appears that house fly and flea eggs are similar in susceptibility to linalool. Linalool applied topically to last instar fly larvae caused no mortality at the highest dose tested (40 $\mu g$/larvae). Although the fly and flea larvae results cannot be directly compared, because of differences in treatment procedures, these results indicate that flea larvae are more sensitive than fly larvae to linalool.

Adult fleas exposed to 130 $\mu g$ linalool/cm² are affected very quickly, viz., 84% mortality at 5 minutes and 100% dead at 10 minutes. At 65 $\mu g/cm^2$, the mortality rate was slower but all were killed at 24 hours. At 26 $\mu g/cm^2$, a few fleas that were completely motionless and considered dead at 60 minutes recovered at 24 hours. Addition of piperonyl butoxide (0.5%) to 26 $\mu g$ linalool/cm² produced higher mortalities at all time intervals and prevented recovery. The mortality patterns of 65 $\mu g$ linalool/cm² and 26 $\mu g$ linalool/cm²+piperonyl butoxide are similar, which indicates that piperonyl butoxide synergized linalool by a factor of 2.5. A 0.5% piperonyl butoxide control produced no mortality.

Treatment of Flea Infested Cats with Linalool

Infested cats were "dipped" in one of the following linalool compositions: 1.0%, 0.5%, and 0.5% +MGK-264 synergist. This synergist was used because both it and piperonyl butoxide prevented recovery of immobilized fleas and increased the toxicity of linalool. Cats "dipped" in linalool exhibited no ill effects. The 1.0% dip and the 0.5% dip with synergist were both 100% effective as all fleas were eliminated from 3 treated animals. The residual activity of linalool was evaluated by re-infesting a flea-free cat 8 days after treating it with 1.0% linalool. No residual activity was observed.

The action of linalool is rapid. Dead fleas were observed on towels used to dry the cats and were found on surfaces under the cats within 15 minutes, and animals were free from fleas the next day.

Linalool has several desirable characteristics as a flea and tick pesticide. It is more toxic to adult fleas than is D-limonene, a registered natural product for flea control on dogs and cats. Although linalool is less toxic to adult fleas than synthetic insecticides currently in use to treat homes, this is not a limiting factor because it is relatively safe to vertebrates and therefore can be used at concentrations higher than those of conventional insecticides. Because of its ovicidal and larvacidal activities, and its low vertebrate toxicity, linalool is useful for treatment of areas in the home where flea eggs and larvae are present.

CONTACT ACTIVITY OF LINALOOL, D-LIMONENE AND α-TERPINEOL AGAINST ADULT FLEAS

In this experiment, the fleas were put for 10 minutes on filter paper moistened with the toxicant at the selected concentration and then transferred to untreated dishes. 4.0%, 3.0%, 2.0% and 1.0% concentrations of D-limonene, linalool, and α-erpineol were evaluated (Table 12).

Under these test conditions, 4% concentrations of D-limonene, linalool and α-terpineol all killed all the fleas. At 3% concentrations, both linalool and α terpineol gave 100% mortality but D-limonene did not. Only linalool killed all the fleas at 2% concentration.

Once the fleas became completely motionless, they did not recover at the higher concentrations (4% and At 2%, there was recovery with α-terpineol (93% motionless at 60 min. and 61% at 24 hr.) but not with D-limonene or linalool. At 1%, there was a slight recovery rate with linalool and α-terpineol but not with D-limonene.

TABLE 12

Mortality of fleas after ten minutes exposure to D-limonene, linalool, and α-terpineol

| Treatment | Percentage fleas that were completely motionless[a] | | | | | |
|---|---|---|---|---|---|---|
| | 5 min | 10 min | 15 min | 20 min | 60 min | 24 hrs |
| 4% D-limonene | 37 | 89 | 96 | 96 | 96 | 100 |
| 4% linalool | 57 | 93 | 93 | 97 | 100 | 100 |
| 4% α-terpineol | 7 | 63 | 93 | 100 | 100 | 100 |
| 3% D-limonene | 10 | 53 | 90 | 83 | 83 | 87 |

TABLE 12-continued

Mortality of fleas after ten minutes exposure to D-limonene, linalool, and α-terpineol

| Treatment | Percentage fleas that were completely motionless[a] | | | | | |
|---|---|---|---|---|---|---|
|  | 5 min | 10 min | 15 min | 20 min | 60 min | 24 hrs |
| 3% linalool | 69 | 96 | 96 | 96 | 100 | 100 |
| 3% α-terpineol | 62 | 96 | 96 | 96 | 100 | 100 |
| 2% D-limonene | 3 | 31 | 44 | 44 | 50 | 72 |
| 2% linalool | 88 | 90 | 100 | 100 | 100 | 100 |
| 2% α-terpineol | 0 | 64 | 64 | 82 | 93 | 61 |
| 1% D-limonene | 0 | 20 | 27 | 30 | 47 | 63 |
| 1% linalool | 20 | 84 | 88 | 100 | 84 | 72 |
| 1% α-terpineol | 0 | 43 | 97 | 97 | 97 | 90 |

[a]Surface treatment formulations

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating an area infested with ticks or fleas, which comprises applying to the infested area an amount of linalool effective to kill the infesting ticks or fleas.

2. The method according to claim 1, wherein the linalool is applied in the form of a liquid pesticidal composition.

3. The method according to claim 1, wherein the linalool is the only pesticidal ingredient applied to the affected area.

4. The method according to claim 2, wherein the linalool is applied in the form of an ethanolic or aqueous liquid pesticidal composition.

5. The method according to claim 1, wherein the linalool is applied in admixture with about 0.25 to about 0.50% of an insecticidal synergist.

6. The method according to claim 1, wherein the infested area is the coat of an animal.

7. The method according to claim 6, wherein the pesticidal composition is applied thereto as a spray, an aqueous dip or a shampoo.

8. The method according to claim 6, wherein the animal is a dog or cat.

9. The method according to claim 8, wherein the pesticidal composition is applied thereto as a spray, an aqueous dip or a shampoo.

10. The method according to claim 9, wherein the pesticidal composition is applied to the coat of the animal as a spray containing 0.1-15% linalool.

11. The method according to claim 9, wherein the pesticidal composition is applied to the coat of the animal as a shampoo containing about 0.5% to about 10% linalool.

12. The method according to claim 9, wherein the pesticidal composition is applied to the coat of the animal as a dip containing 0.3-2.5% linalool.

13. The method according to claim 1, wherein the infested area is a room infested with fleas and which contains bedding, carpet or furniture to which is applied a pesticidal composition containing 0.1-15% linalool.

14. The method according to claim 11, wherein the room contains a carpet to which the pesticidal composition is applied thereto as a spray containing about 1% to about 15% linalool.

* * * * *